United States Patent [19]

Cumbo et al.

[11] Patent Number: 4,680,259
[45] Date of Patent: Jul. 14, 1987

[54] ANALYTICAL ELEMENT AND METHOD FOR COLORIMETRIC DETERMINATION OF TOTAL CHOLESTEROL

[75] Inventors: Peter E. Cumbo; Robert F. Fricker, both of Rochester, N.Y.

[73] Assignee: Eastman Kodak Company, Rochester, N.Y.

[21] Appl. No.: 654,590

[22] Filed: Sep. 26, 1984

[51] Int. Cl.$^4$ .......................... C12Q 1/60; C12Q 1/28; C12Q 1/44

[52] U.S. Cl. ........................................ 435/11; 422/56; 435/19; 435/25; 435/28; 435/805

[58] Field of Search ..................... 435/11, 19, 25, 28, 435/805; 422/56, 57

[56] References Cited

U.S. PATENT DOCUMENTS

| | | | |
|---|---|---|---|
| 3,869,349 | 3/1975 | Goodhue et al. | 435/11 |
| 3,983,005 | 9/1976 | Goodhue et al. | 435/11 |
| 4,042,329 | 8/1977 | Hochstrasser | 436/71 |
| 4,186,251 | 1/1980 | Tarbutton | 435/11 |
| 4,275,151 | 6/1981 | Esders et al. | 435/11 |
| 4,275,152 | 6/1981 | Esders et al. | 435/11 |
| 4,291,121 | 9/1981 | Acquati et al. | 435/10 |
| 4,312,834 | 12/1982 | Vogel et al. | 436/66 |
| 4,378,429 | 3/1983 | Modrovich | 435/11 |
| 4,409,326 | 10/1983 | Modrovich | 435/11 |
| 4,503,144 | 3/1985 | Deeg et al. | 435/11 |
| 4,503,146 | 3/1985 | Yun et al. | 435/19 |

OTHER PUBLICATIONS

Wiebe et al., *Clin. Chem.*, 30(3), pp. 352–356 (1984).
Kodak Publication MP2-35, 1983 entitled "Kodak EKTACHEM Clinical Chemistry Products Test Methodology for Cholesterol Analysis."
*Research Disclosure* 201005, published Dec. 20, 1980 (Abstract).

*Primary Examiner*—Sidney Marantz
*Attorney, Agent, or Firm*—J. Lanny Tucker

[57] ABSTRACT

An analytical element is designed for the colorimetric determination of total cholesterol in aqueous liquids, such as biological fluids. This element comprises an absorbent material and critical amounts of cholesterol ester hydrolase (from about 1500 to about 12,000 I.U./m$^2$) and a nonionic surfactant (from about 5 and up to, but less than 11 g/m$^2$). The use of these ranges of reagents reduces the potential for interference by triglycerides present in a test sample. Total cholesterol is determined with this element by detection of a color change resulting from a series of enzymatic reactions which produce hydrogen peroxide.

20 Claims, No Drawings

ANALYTICAL ELEMENT AND METHOD FOR COLORIMETRIC DETERMINATION OF TOTAL CHOLESTEROL

FIELD OF THE INVENTION

The present invention relates to an enzymatic assay for total cholesterol. In particular, it relates to an improved analytical element, and methods of making and using such for determination of total cholesterol in biological fluids, such as human blood serum.

BACKGROUND OF THE INVENTION

It is fairly well established that the cholesterol content of whole blood is directly related to certain ailments in humans and animals. Among these ailments are hepatocellular diseases, thyroid metabolism diseases, biliary obstruction, and atherosclerosis and other vascular difficulties. Cholesterol is found in blood in either its free form or in the form of its ester. Free cholesterol refers to cholesterol in its unreacted state. Total cholesterol refers to the sum of free cholesterol and its ester derivatives. Cholesterol is found in constant amounts in serum under normal conditions. In general, 25% of the total cholesterol level in serum is free cholesterol while the remaining 75% is in the form of ester derivatives.

Known quantitative analyses of total cholesterol involve the use of enzymes to convert both free cholesterol and cholesterol esters into detectable products. This enzymatic method uses the following series of reactions involving cholesterol esterase, cholesterol oxidase and peroxidase.

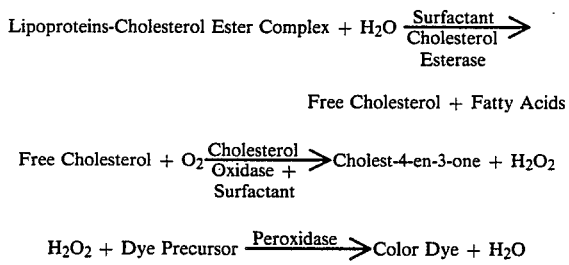

In the first reaction, it is essential that all of the cholesterol esters are hydrolyzed to free cholesterol. This can be accomplished with a primary hydrolyzing reagent which is an enzyme having cholesterol esterase activity. This enzyme is known in the art as lipase, esterase or cholesterol ester hydrolase. However, it has been reported by Wiebe et al in *Clin. Chem.*, 30(3), pp. 352–356 (1984) and references cited therein that incomplete hydrolysis can occur thereby giving inaccurately low cholesterol determinations. Many attempts have been made to augment ester hydrolysis by adding biliary cofactors, protease or nonionic surfactants (e.g. the TRITONs available from Rohm & Haas, Philadelphia, Pa.).

A recent advance in the clinical chemistry art is a multilayer analytical element for the determination of total cholesterol manufactured by Eastman Kodak Company (Rochester, N.Y.) under the label of EKTA-CHEM Clinical Chemistry Slide (CHOL) and described in Kodak Publication MP2-35, 1983 entitled "Kodak EKTACHEM Clinical Chemistry Products Test Methodology for Cholesterol Analysis." This element contains reagents which hydrolyze cholesterol esters and determine total cholesterol in the test sample. For example, it contains about 540 I.U./m$^2$ of cholesterol ester hydrolase and about 11 g/m$^2$ of a nonionic surfactant.

It has been observed, however, that the described element is sensitive to fluctuating levels of triglycerides present in the serum sample. For example, elevated triglyceride levels can positively bias the total cholesterol determination. User attempts to minimize this effect involve dilution procedures which are time-consuming and subject to additional error.

Merely adding increased amounts of a single reagent to the element does not eliminate the adverse effect of the triglycerides because of the multiple reactions used in the assay. Hence, there is a need in the art for a means for determining total cholesterol in a liquid sample which is not adversely affected by the amount of triglycerides in the sample.

SUMMARY OF THE INVENTION

The present invention provides a means for rapid and precise total cholesterol determination in aqueous liquids. The assay of this invention is not adversely affected by the presence of triglycerides in the test sample. Hence, the present invention avoids the problems encountered with conventional assays. In addition, the present invention provides an element with improved keeping and coating-to-coating reproducibility.

These significant improvements in clinical chemistry are accomplished by use of an improved analytical element which contains critical amounts of reagents. We have found that using these amounts of cholesterol ester hydrolase and the nonionic surfactant reduces the effect of triglycerides by 50% or more. In a preferred embodiment, the amounts of peroxidase and/or cholesterol oxidase are also adjusted to improve the element even further. Element keeping and coating-to-coating reproducibility are also improved with this invention.

Therefore, in accordance with this invention, an analytical element for the colorimetric determination of total cholesterol in an aqueous liquid comprises an absorbent material, and contains a peroxidative substance,
a colorimetric composition which, in the presence of hydrogen peroxide and the peroxidative substance, produces a color change,
cholesterol oxidase,
a nonionic surfactant present in an amount of from about 5 and up to, but less than 11 g/m$^2$, and
cholesterol ester hydrolase present in an amount of from about 1500 to about 12,000 I.U./m$^2$.

This invention also provides a method for providing the analytical element just described, which element has a reduced potential for interference by triglycerides upon determination of total cholesterol, and comprises an absorbent material. This method comprises incorporating into the absorbent material a peroxidative substance, a colorimetric composition which, in the presence of hydrogen peroxide and the peroxidative substance, produces a color change, cholesterol oxidase, a nonionic surfactant in an amount to provide from about 5 and up to, but less than 11 g/m$^2$, and cholesterol ester hydrolase in an amount to provide from about 1500 to about 12,000 I.U./m$^2$.

Further, a method for the colorimetric determination of total cholesterol in an aqueous liquid comprises the steps of:

A. contacting a sample of the liquid with the analytical element described above to produce a color change, and B. detecting the color change.

DETAILED DESCRIPTION OF THE INVENTION

This invention provides an analytical element for the determination of total cholesterol in aqueous liquids, such as biological fluids. Biological fluids which can be so assayed include human and animal whole blood, blood serum, plasma, feces, etc. In the context of this disclosure, determination means either qualitative (i.e. merely detection), semi-quantitative or quantitative analysis unless otherwise specified.

This assay is an enzymatic assay utilizing the sequence of reactions noted above in the Background of the Invention. The principal reagents utilized in the assay include cholesterol ester hydrolase, cholesterol oxidase, a nonionic surfactant, a peroxidative substance and a colorimetric composition.

Cholesterol ester hydrolase (hereinafter CEH) is present in the element of this invention in an amount of from about 1500 to about 12,000 I.U./m$^2$ as opposed to about 540 I.U./m$^2$ in the conventional element described above. In the context of this disclosure, I.U. represents the International Unit for enzyme activity defined as one I.U. being the amount of enzyme activity required to catalyze the conversion of 1 micromole of substrate per minute under standard pH and temperature conditions for the given enzyme. CEH activity is determined as described below. CEH is an enzyme which catalyzes the hydrolysis of cholesterol esters into free cholesterol. CEH is also known in the art as cholesterol esterase or as lipase. CEH is preferably present in the element at a coverage of from about 2000 to about 9000 I.U./m$^2$ and more preferably from about 2500 to about 7000 I.U./m$^2$ for optimum advantage.

CEH is either commercially available, or can be readily prepared from plant or microbial sources using manufacturing techniques known in the art as described, for example, in U.S. Pat. No. 4,275,151 (issued June 23, 1981 to Esders et al).

Elements of this invention also include a nonionic surfactant in an amount of from about 5 and up to, but less than 11 g/m$^2$, and preferably at a coverage of from about 6 to about 8 g/m$^2$, as opposed to 11 g/m$^2$ or more in the conventional element described above. At the new level of surfactant, the hydrolysis of cholesterol esters appears to be complete while the other reactions employed in the assay are not inhibited to a significant degree. The nonionic surfactants particularly useful include alkyl phenoxy polyethoxy ethanols which are commercially available under the TRITON trademark from Rohm and Haas Company (Philadelphia, Pa.). Preferred alkyl phenoxy polyethoxy ethanols comprise a polyoxyethylene chain of less than about 20 oxyethylene units and have 8 or 9 carbon atoms in the alkyl portion. Other useful nonionic surfactants can be determined by one skilled in the art.

At these levels of CEH and nonionic surfactant, the triglyceride effect is significantly reduced while the other enzymatic reactions are also promoted. For example, the triglyceride interference is reduced to less than 40 mg/dl as illustrated in Examples 1-3 hereinbelow.

Cholesterol oxidase (hereinafter COD) is an enzyme used to catalyze the reaction of free cholesterol and oxygen to form cholestenone (also known as cholest-4-en-3-one) and hydrogen peroxide. The coverage of COD in the element can be varied widely, but generally it is present in the element at a coverage of at least about 2000 I.U./m$^2$, and preferably from about 2400 to about 4000 I.U./m$^2$. COD is either commercially available or it can be readily prepared from microbial sources using known fermentation techniques described in, for example, *Research Disclosure*, Vol. 126, pp. 46-50 (1974), *Methods in Enzymology*, Vol. 1, Academic Press, New York, p. 678 (1955), *J. Biol. Chem.*, 206, 511 (1954), and German Patent No. 2,246,695, (published Mar. 26, 1973). *Research Disclosure* is a publication available from Kenneth Mason Publications, Ltd., The Old Harbourmaster's, 8 North Street, Emsworth, Hampshire P010 7DD England.

Total cholesterol is determined according to the practice of this invention by using a colorimetric composition which provides a color change upon reaction with hydrogen peroxide generated from the oxidation of free cholesterol. A peroxidative substance is used to catalyze this peroxide reaction. A peroxidative substance is a substance which exhibits peroxidase-like or peroxidative activity. That is, it is a compound which has the ability to catalyze the oxidation of another substance by means of hydrogen peroxide or another peroxide. Peroxidase is a preferred peroxidative substance in the practice of this invention. Peroxidases are generally conjugated proteins containing iron porphyrin. It is either commercially available or can be readily obtained from various plant or microbial sources using known manufacturing procedures. Certain synthetic peroxidases are also useful in the practice of this invention, as well as hemin, methemoglobin, oxyhemoglobin, hemoglobin, hemochromogen, alkaline hematin, hemin derivatives, iron sulfocyanate, iron tannate, ferrous ferrocyanide, chromic salts, and the like. Although the amount can be varied, the peroxidative substance is generally present in the element in an amount which is equivalent to at least 40,000 I.U./m$^2$ of peroxidase activity, and preferably at a coverage of from about 60,000 to about 160,000 I.U./m$^2$ peroxidase equivalent activity. In other words, if a nonenzyme peroxidative substance is used, the coverage in g/m$^2$ is such to provide peroxidative activity equivalent to the indicated enzyme activity.

Any suitable colorimetric composition which will produce a detectable color change in the presence of hydrogen peroxide and a peroxidative substance can be used in the practice of this invention. Representative materials which can be so used include the following substances with a color coupler where necessary:

monoamines, such as aniline and its derivatives, diamines, such as o-phenylenediamine, benzidine, etc., phenols, such as phenol, thymol, cresols, naphthols, etc., polyphenols, such as catechol, guaiacol, pyrogallol, etc., aromatic acids, such as salicyclic acid, gallic acid, etc., leuco dyes, such as leucomalachite green, triarylimidazoles as described in U.S. Pat. No. 4,089,747 (issued May 16, 1978 to Bruschi) and triarylmethanes, including those described in copending and commonly assigned U.S. patent application Ser. No. 612,509, filed May 21, 1984 in the names of B. E. Babb and D. S. Daniel, etc., colored dyes such as 2,6-dichlorophenolindophenol, various biological substances such as epinephrine, flavones, tyrosine, etc., and others known to one skilled in clinical chemistry.

Particularly useful colorimetric compositions are the leuco dyes noted above, and especially the triarylimidazoles described in the Bruschi patent. Other preferred colorimetric compositions include a color-forming coupler which can react with an oxidizable color developing compound to give a color change. Useful color-forming couplers include substituted anilines (i.e. toluidines) including those described in, for example, U.S. Pat. Nos. 4,251,629 (issued Feb. 17, 1981 to Yamanisi et al), 4,260,679 (issued Apr. 7, 1981 to Tsuda et al) and 4,396,714 (issued Aug. 2, 1983 to Maeda et al), Japanese Patent Publication No. 83/22200 (published May 7, 1983), European Patent Application No. 68,356 (published Jan. 5, 1983), U.K. Patent No. 2,107,863 (published Oct. 22, 1981), and Japanese Patent Publication 58/898 (published Jan. 6, 1983). Representative oxidizable developing compounds include benzidine and its homologs, p-phenyldiamines, p-aminophenols, aminoantipyrines, e.g. 4-aminoantipyrine, and the like. A preferred developing compound is 4-aminoantipyrine.

In the context of this application, the term "color change" refers to the situation either where a color is generated where there was no color, where a color shift occurs from one color to another, or where a pre-existing color is diminished or disappears entirely. Generally, the color change is due to the formation of a color dye where there previously was no color.

Since the enzymes used in this invention operate most efficiently within a relatively narrow pH range, it is generally preferred to incorporate buffers in the element in an amount sufficient to maintain the element environment at the appropriate pH during the assay, i.e. when contacted with the sample of liquid. Generally, for this invention, the element contains buffers in an amount sufficient to maintain the pH at from about 5.5 to about 9.5, and preferably from about 5.5 to about 6.5 during the assay. The useful amounts are easily determined by one skilled in the art. Techniques for achieving the desired buffering are known in the art and involve dissolving or dispersing appropriate amounts of the buffer in the coating composition prior to coating. Suitable buffers include phosphates, borates, tris buffers, and others known in the art as described, e.g. in *Biochem.*, 5, 467 (1966).

Other addenda known to one skilled in the art can be incorporated into the elements of this invention to improve manufacturability, sample spreading, etc. if desired.

The dry analytical element of this invention can be a self-supporting absorbent material, i.e. a thin sheet of self-supporting absorbent or bibulous material, such as filter paper or a paper strip, which contains the reagents described herein. Such elements are known in the art as test strips, diagnostic elements, dip sticks, diagnostic agents and the like.

The reagents, individually or in any combination can be incorporated into a suitable absorbent material by imbibition or impregnation, or can be coated thereon. Useful absorbent materials are insoluble and maintain their structural integrity when exposed to water or physiological fluids such as serum. Useful absorbent materials can be prepared from paper, porous particulate structures, porous polymeric films, cellulose, wood, glass fiber, woven and nonwoven fabrics (synthetic and nonsynthetic) and the like. A useful dry analytical element is made by imbibing a solution of the reagents into the material and drying. Useful materials and procedures for making such elements are well known in the art as exemplified in U.S. Pat. Nos. 3,092,465 issued June 4, 1963 to Adams et al), 3,802,842 (issued Apr. 9, 1974 to Lange et al), 3,915,647 (issued Oct. 28, 1975 to Wright), 3,917,453 (issued Nov. 4, 1975 to Milligan et al), 3,936,357 (issued Feb. 3, 1976 to Milligan et al), 4,186,251 (issued Jan. 29, 1980 to Tarbutton), 4,248,829 (issued Feb. 3, 1981 to Kitajima et al), 4,255,384 (issued Mar. 10, 1981 Kitajima et al), 4,270,920 (issued June 2, 1981 to Kondo et al), 4,291,121 (issued Sept. 22, 1981 to Acquati et al) and 4,312,834 (issued Jan. 26, 1982 to Vogel et al), and U.K. Patent No. 2,052,057 (published Jan. 21, 1981).

Preferably, the dry analytical elements of this invention have at least one porous spreading zone. This zone can be a self-supporting absorbent material (i.e. composed of a material rigid enough to maintain its integrity), but preferably it is carried on a separate supporting substrate (commonly called a support). Such a support can be any suitable dimensionally stable, and preferably, transparent (i.e. radiation transmissive) material which transmits electromagnetic radiation of a wavelength between about 200 and about 900 nm. A support of choice for a particular element should be compatible with the intended mode of detection (reflection or transmission spectroscopy). Useful support materials include paper, metal foils, polystyrene, polyesters [e.g. poly(ethylene terephthalate)], polycarbonates, cellulose esters (e.g. cellulose acetate), etc.

The porous spreading zone can be prepared from any suitable fibrous or non-fibrous material or mixtures of either or both. The void volume and average pore size of this zone can be varied depending upon the use intended. For example, if whole blood or other liquid samples containing high molecular weight materials are to be assayed, the void volume and average pore size are generally greater than if serum is to be assayed.

Useful spreading zones can be prepared using fibrous materials, either mixed with a suitable binder material or woven into a fabric, as described in U.S. Pat. No. 4,292,272 (issued Sept. 29, 1981 to Kitajima et al). Alternatively the spreading zone is prepared from polymeric compositions (e.g. blush polymers) or particulate materials, with or without binding adhesives, as described in U.S. Pat. Nos. 3,992,158 (issued Nov. 16, 1976 to Przybylowicz et al) and 4,258,001 (issued Mar. 24, 1981 to Pierce et al). Other useful spreading zone materials are described in W. German OLS No. 3,150,102 (published July 29, 1982) and Japanese Patent Publication No. 57(1982)-101760 (published June 24, 1982), both assigned to Konishiroku Photo. It is desirable that the spreading zone be isotropically porous, meaning that the porosity is the same in each direction in the zone as created by interconnected spaces or pores between particles, fibers, polymeric strands, etc.

The elements can have one or more reagent zones, spreading zones, registration zones, radiation-blocking or filter zones, subbing zones, hydrophilic binder zones, barrier zones, buffer zones, etc. The zones are generally in fluid contact with each other meaning that fluids, reagents and reaction products can pass between superposed regions of adjacent zones. Stated in another manner, fluid contact refers to the ability to transport components of a fluid between the zones in fluid contact. Preferably, the zones are separately coated layers, although two or more zones can be a single layer, or a zone can contain two or more separate layers.

In a preferred embodiment, the analytical element of this invention comprises a support having thereon, in order and in fluid contact, a hydrophilic binder layer and a spreading/reagent layer. The hydrophilic binder layer generally comprises one or more hydrophilic binders (naturally occurring or synthetic colloids or polymers) one or more buffers, one or more surfactants and, optionally, other addenda known in the art. Gelatin is a preferred hydrophilic binder, although many others are also suitable. An optional subbing layer containing conventional subbing materials can be incorporated between the other layers to improve manufacturability and layer adhesion. In this embodiment, all of the reagents used in the enzymatic reactions of the assay are incorporated into the spreading/reagent layer.

In the multizone elements of this invention, the reagents and other addenda can be incorporated by imbibition into already coated layers or by coating them in the layer coating composition. All of these techniques are known in the art.

A variety of different elements, depending on the method of assay, can be prepared in accordance with the present invention. The elements can be configured in a variety of forms, including elongated tapes of any desired width, sheets, slides or chips.

The assay of this invention can be manual or automated. In general, total cholesterol determination is made by taking the element from a supply roll, chip packet or other source and physically contacting it with a sample (e.g. 1–20 μl) of the liquid to be assayed. Such contact can be accomplished in any suitable manner, e.g. dipping or immersing the element into the sample or, preferably, by spotting the element by hand or machine with a drop of the sample with a suitable dispensing means.

After sample application, the element is exposed to any conditioning such as incubation, heating or the like, that may be desirable to quicken or otherwise facilitate obtaining a test result.

Determination of total cholesterol is achieved when the color change which occurs (e.g. formation of a color dye) is detected. This change can be detected with the unaided eye or with suitable spectrophotometric means and procedures. Generally, with color dye measurement, the absorbance of the dye is measured at or near its absorption peak ($\lambda_{max}$), although it may be advantageous to "read off the peak" in some instances. The absorbance can be determined from either transmission or reflectance density, depending upon the format of the element and spectrophotometric means.

In the following examples provided to illustrate the practice of the invention, the materials used were obtained as follows: peroxidase from Miles Laboratories (Elkhart, Ind.), cholesterol ester hydrolase from Enzyme Development Corp. (New York, N.Y.), cholesterol oxidase from Upjohn Corporation (Kalamazoo, Mich.), polyurethane resin from B. F. Goodrich (Cleveland, Ohio), TRITON X-100 and TRITON X-200E alkylaryl polyether sulfonate surfactant from Rohm and Haas (Philadelphia, Pa.), and SURFACTANT 10G (P-nonylphenoxy) glycerol surfactant from Olin Mathieson Co. (Stamford, Conn.). All other reagents and materials were either prepared in house using conventional procedures or obtained from Eastman Organic Chemicals (Rochester, N.Y.).

In the context of this invention, the activity of cholesterol ester hydrolase (CEH) can be determined by the following general procedure:

A substrate solution is prepared with gentle stirring and warming with 200 mg of cholesteryl linoleate (mol. wt. 647, available as Catalog No. 10605 from Eastman Organic Chemicals, Rochester, N.Y.), 5 ml TRITON X-100 alkyl phenoxy polyethoxy ethanol surfactant and 95 ml of deionized water.

A CEH enzyme solution is prepared by adding 5 mg enzyme to 1 ml of deionized water.

A reagent solution sample is prepared by mixing 0.1 ml of the substrate solution, 2.5 ml of 0.05 molar phosphate buffer (pH 7), 0.038 ml of peroxidase solution (5 mg/ml $H_2O$), 0.015 ml of cholesterol oxidase solution (6 mg/ml $H_2O$), 0.04 ml of dimethoxybenzidine dihydrochloride (5 mg/ml $H_2O$) and deionized water up to a 3 ml volume.

Four reagent solution samples (3 ml each) are warmed at 37° C. for 5 minutes and background absorbance is measured at 430 nm with a conventional spectrophotometer. The CEH enzyme solution is diluted 1:20 with deionized water.

An aliquot (25 μl) of the diluted CEH enzyme solution is added to each reagent solution sample to make 4 test samples, and the absorbance of the resulting dye color change is measured in each test sample for 12 minutes at 430 nm with the conventional spectrophotometer.

During the last five minutes of the assay, the change in absorbance ($\Delta A$) is measured and activity (u/mg) is determined according to the equation:

$$u/mg = \frac{(\Delta A/\text{min}) \, (\text{sample vol.} = 3 \text{ ml}) \, (\text{dilution} = 20)}{(\text{molar extinction} = 11.3) \, (\text{aliquot size} = 25 \, \mu l) \, (\text{CEH concentration} = 5 \text{ mg/ml})}$$

This activity (u/mg) can be converted to I.U. activity using known calculations. Using this test, the activity of CEH useful in this invention is generally from about 1500 to about 6000 I.U./$m^2$. Using a CEH substrate from another source (e.g. Sigma Chemical Co., St. Louis, Mo.), or using higher amounts of substrate, may change the enzyme activity within the broader range of from about 1500 to about 12,000 I.U./$m^2$.

The activity of other enzymes useful in this invention (peroxidase and cholesterol oxidase) can be determine using conventional procedures.

EXAMPLES 1–3

Comparison of Analytical Elements for Total Cholesterol Determination

These examples compare the improved elements of this invention to a conventional element (Control A) described in Kodak Publication MP2-35 noted above and to a similar Control A' element. The results of the testing show that the elements of this invention have significantly improved properties. They particularly show that the assay for total cholesterol performed according to this invention is negligibly affected by triglycerides present in the test liquid. The Control A element is unacceptably affected by triglycerides in the test solutions.

The elements evaluated had the following format and components. Table I below shows the levels of certain reagents which were different for each element.

| Spreading/Reagent Layer | Coverage |
| --- | --- |
| Peroxidase (POD) | See Table I |
| Cholesterol ester hydrolase (CEH) | " |
| Cholesterol oxidase (COD) | " |
| Potassium phosphate buffer (pH 5.5–6.5) | 1–2 g/m$^2$ |
| TRITON X-100 alkyl phenoxy polyethoxy ethanol nonionic surfactant | See Table I |
| Barium sulfate | 70–140 g/m$^2$ |
| Cellulose acetate | 6–12 g/m$^2$ |
| 5,5-dimethyl-1,3-cyclohexanedione | 0.2–0.6 g/m$^2$ |
| 2-(3,5-dimethoxy-4-hydroxyphenyl)-4,5-bis(4-dimethylaminophenyl)imidazole leuco dye | 0.8–2.4 g/m$^2$ |
| Polyurethane resin | 0.5–1.5 g/m$^2$ |
| Subbing Layer | |
| Poly(n-isopropylacrylamide) | 0.2–0.8 g/m$^2$ |
| Hydrophilic Binder Layer | |
| Gelatin (hardened) | 10–25 g/m$^2$ |
| Potassium phosphate buffer (pH 5.5–6.5) | 0.1–1.7 g/m$^2$ |
| TRITON X-200E alkylaryl polyether sulfonate surfactant | 0.005–0.02 g/m$^2$ |
| SURFACTANT 10G ™ (p-nonylphenoxy) glycerol surfactant | 0.005–0.01 g/m$^2$ |
| Poly(ethylene terephthalate) Support | |

TABLE I

| Element | Coverages | | | Triton X-100* |
| --- | --- | --- | --- | --- |
| | POD | COD | CEH | |
| Control A | 20,000 I.U./m$^2$ | 2400 I.U./m$^2$ | 540 I.U./m$^2$ | 11 g/m$^2$ |
| 1 | 140,000 I.U./m$^2$ | " | 1620 I.U./m$^2$ | 6.5 g/m$^2$ |
| Control A' | " | " | 3780 I.U./m$^2$ | 11 g/m$^2$ |
| 2 | " | " | 3780 I.U./m$^2$ | 6.5 g/m$^2$ |
| 3 | 100,000 I.U./m$^2$ | 3000 I.U./m$^2$ | 2700 I.U./m$^2$ | 8.5 g/m$^2$ |

*alkyl phenoxy polyethoxy ethanol nonionic surfactant

The elements were evaluated in the following manner. Human serum previously determined by the Abell-Kendall method (*J. Biol. Chem.*, 195, p. 357, 1952) to contain about 480 mg/dl of total cholesterol was divided into two fractions (I and II). Into Fraction I, about 250 mg/dl of triglycerides was added. Into Fraction II, about 950 mg/dl triglycerides was added. Ten microliter aliquot samples of each fraction were individually applied to the spreading/reagent layer of each element and were analyzed using an EKTACHEM clinical chemistry analyzer (available from Eastman Kodak Co., Rochester, N.Y.) using conventional procedures (reflection density observed at 540 nm).

The cholesterol determination of Fraction I was subtracted from that of Fraction II for each element. The difference was identified as Δ cholesterol (mg/dl) and is a measure of the effect of high triglycerides on the assay. These values are shown in Table II below.

These tests were also performed using two serum samples, each containing about 360 mg/dl cholesterol, and about 100 and about 400 mg/dl triglycerides, respectively, using the same elements. The Control A element determination of cholesterol was adversely affected by the presence of triglycerides while the determination using elements of this invention were not.

TABLE II

| Element | Δ Cholesterol (mg/dl) |
| --- | --- |
| Control A | 89 |
| 1 | 24 |
| Control A$^1$ | 14 |
| 2 | 2 |
| 3 | 5 |

EXAMPLE 4-

Improved Coating-to-Coating Reproducibility in Elements of this Invention

This example illustrates the improved coating-to-coating reproducibility obtained with the elements of this invention as compared to the conventional element described above in the Background of the Invention.

Two analytical elements were prepared according to the present invention having a format similar to that in Examples 1–3. Two other elements were also prepared similar to the Control A element of the previous examples. All elements were individually spotted with several conventional calibrator solutions containing various amounts of cholesterol and triglycerides. Cholesterol was determined in each element with an EKTACHEM analyzer as described above.

The elements of this invention exhibited improved coating-to-coating reproducibility as shown by very small differences in the cholesterol assay values between the two invention elements. However, the two Control elements showed marked differences in cholesterol assay values, indicating poorer coating-to-coating reproducibility.

EXAMPLE 6

Several analytical elements were prepared similar to those described in Examples 1–3, except that they contained different amounts of cholesterol ester hydrolase and TRITON X-100 alkyl phenoxy polyethoxy ethanol nonionic surfactant as shown in Table III below. The Control elements had reagent level(s) outside the scope of this invention. In those elements, only one reagent was changed compared to two reagents in the element of this invention.

The elements were tested as described in Examples 1–3 using a serum sample comprising about 600 mg/dl cholesterol and about 250 mg/dl triglycerides, and the reflection density ($D_R$) was determined with an EKTACHEM analyzer after 10 minutes. As shown in Table III below, the $D_R$ of the Control elements was significantly lower, implying that the reactions of assay was incomplete. The assay of the element of this invention provided a higher $D_R$, indicating a completion of the enzymatic reactions necessary for total cholesterol determination.

TABLE III

| Element | CEH (I.U./m$^2$) | TRITON X-100* (g/m$^2$) | $D_R$ (at 540 nm) |
| --- | --- | --- | --- |
| Example 5 | 6000 | 8 | 1.67 |
| Control A | 540 | 11 | 1.46 |
| Control B | 1620 | 11 | 1.33 |
| Control C | 3780 | 11 | 1.35 |
| Control D | 540 | 6.5 | 1.27 |
| Control E | 540 | 8 | 1.44 |

*alkyl phenoxy polyethoxy ethanol nonionic surfactant

The invention has been described in detail with particular reference to preferred embodiments thereof, but it will be understood that variations and modifications can be effected within the spirit and scope of the invention.

We claim:

1. An analytical element for the colorimetric determination of total cholesterol in an aqueous liquid, said element comprising an absorbent material, and containing a peroxidative substance in an amount equivalent to a peroxidase activity of at least 40,000 I.U./m$^2$, a colorimetric composition which, in the presence of hydrogen peroxide and said peroxidative substance, produces a color change, cholesterol oxidase, a nonionic surfactant present in an amount of from about 5 and up to, but less than 11 g/m$^2$, and cholesterol ester hydrolase present in an amount of from about 1500 to about 12,000 I.U./m$^2$.

2. The element of claim 1 wherein said cholesterol oxidase is present in an amount of at least about 2000 I.U./m$^2$.

3. The element of claim 1 containing said nonionic surfactant in an amount of from about 6 to about 8 g/m$^2$.

4. The element of claim 1 wherein said absorbent material is an isotropically porous spreading zone carried on a support.

5. A multilayer analytical element for the colorimetric determination of total cholesterol in an aqueous liquid, said element comprising a support having thereon, in order and in fluid contact, a hydrophilic binder layer and a spreading/reagent layer containing a peroxidative substance present in an amount equivalent to a peroxidase activity of from about 60,000 to about 160,000 I.U./m$^2$, a colorimetric composition which, in the presence of hydrogen peroxide and said peroxidative substance, produces a color dye, cholesterol oxidase present in an amount of from about 2400 to about 4000 I.U./m$^2$, a nonionic surfactant present in an amount of from about 5 and up to, but less than 11 g/m$^2$, and cholesterol ester hydrolase present in an amount of from about 1500 to about 12,000 I.U./m$^2$.

6. The element of claim 5 wherein said surfactant is an alkyl phenoxy polyethoxy ethanol.

7. The element of claim 5 wherein said peroxidative substance is peroxidase, said surfactant is present in an amount of from about 6 to about 8 g/m$^2$, and said cholesterol ester hydrolase is present in an amount of from about 2500 to about 7000 I.U./m$^2$.

8. The element of claim 5 wherein said colorimetric composition comprises a leuco dye.

9. The element of claim 5 wherein said colorimetric composition comprises a color-forming coupler and an oxidizable color developing compound which is capable of reacting with said coupler to produce a color dye.

10. The element of claim 5 comprising a buffer effective to maintain the pH of the element at from about 5.5 to about 9.5.

11. The element of claim 5 comprising a subbing layer between said binder and spreading/reagent layers.

12. A method for providing an analytical element for the determination of total cholesterol in an aqueous liquid, said element having a reduced potential for interference by triglycerides upon said determination and comprising an absorbent material, said method comprising incorporating into said element a peroxidative substance in an amount equivalent to a peroxidase activity of at least 40,000 I.U./m$^2$, a colorimetric composition which, in the presence of hydrogen peroxide and said peroxidative substance, produces a color change, cholesterol oxidase, a nonionic surfactant in an amount to provide from about 5 and up to, but less than 11 g/m$^2$, and cholesterol ester hydrolase in an amount to provide from about 1500 to about 12,000 I.U./m$^2$.

13. A method for the colorimetric determination of total cholesterol in an aqueous liquid, said method comprising the steps of:

A. contacting a sample of said liquid with the analytical element of claim 1 to produce a color change, and B. detecting said color change.

14. The method of claim 13 wherein said element comprises said peroxidative substance in an amount equivalent to a peroxidase activity of from about 60,000 to about 160,000 I.U./m$^2$, and cholesterol oxidase in an amount of from about 2400 to about 4000 I.U./m$^2$.

15. The method of claim 13 wherein said element comprises an alkyl phenoxy polyethoxy ethanol nonionic surfactant.

16. A method for the colorimetric determination of total cholesterol in an aqueous liquid, said method comprising the steps of:

A. contacting a sample of said liquid with the multilayer analytical element of claim 5 to produce a color dye, and B. detecting said color dye.

17. The method of claim 16 wherein said element comprises peroxidase, said surfactant in an amount of from about 6 to about 8 g/m$^2$, and cholesterol ester hydrolase in an amount of from about 2500 to about 7000 I.U./m$^2$.

18. The method of claim 16 wherein said colorimetric composition comprises a leuco dye.

19. The method of claim 16 wherein said colorimetric composition comprises a color-forming coupler and an oxidizable color developing compound which is capable of reacting with said coupler to produce a color dye.

20. The method of claim 16 which is carried out at a pH of from about 5.5 to about 9.5.

* * * * *

UNITED STATES PATENT OFFICE
CERTIFICATE OF CORRECTION

PATENT NO. : 4,680,259
DATED : July 14, 1987
INVENTOR(S) : P.E. Cumbo et al

It is certified that error appears in the above-identified patent and that said Letters Patent are hereby corrected as shown below:

Column 9, line 33 the part reading "Triton"
   should read --TRITON--.

Column 10, line 37 the part reading "EXAMPLE 6"
   should read --EXAMPLE 5--.

Signed and Sealed this

Seventeenth Day of November, 1987

Attest:

DONALD J. QUIGG

*Attesting Officer*     *Commissioner of Patents and Trademarks*